United States Patent [19]
Sakano et al.

[11] Patent Number: 5,939,296
[45] Date of Patent: Aug. 17, 1999

[54] PROCESS FOR PRODUCING L-ASPARTIC ACID

[75] Inventors: Koichi Sakano, Frankfurt am Main, Germany; Masaharu Mukouyama, Tsukuba-gun; Takaya Hayashi, Tsuchiura, both of Japan

[73] Assignee: Nippon Shokubai Co., Ltd., Osaka, Japan

[21] Appl. No.: 08/908,717

[22] Filed: Aug. 8, 1997

[30] Foreign Application Priority Data

Aug. 9, 1996 [JP] Japan .................................. 8-211595

[51] Int. Cl.⁶ .......................................................... C12P 7/46
[52] U.S. Cl. .............................................................. 435/145
[58] Field of Search ............................................... 435/145

[56] References Cited

U.S. PATENT DOCUMENTS

| | | | |
|---|---|---|---|
| 3,391,059 | 7/1968 | Takamura et al. | 195/30 |
| 5,541,090 | 7/1996 | Sakano et al. | 435/109 |
| 5,677,156 | 10/1997 | Goto et al. | 435/145 |

FOREIGN PATENT DOCUMENTS

| | | |
|---|---|---|
| 0 588 674 | 3/1994 | European Pat. Off. . |
| 0 736 603 | 10/1996 | European Pat. Off. . |
| 0 798 377 A2 | 10/1997 | European Pat. Off. . |
| 2 619 809 | 3/1989 | France . |
| 38-2793 | 3/1963 | Japan . |
| 38-2794 | 3/1963 | Japan . |
| 5-37631 | 6/1993 | Japan . |
| 8-33491 | 2/1996 | Japan . |
| 8-332092 | 12/1996 | Japan . |
| 10 66591 | 3/1998 | Japan . |

OTHER PUBLICATIONS

Otsuki K –I: "CIS–Trans Isomerase Isomerisation from Maleic Acid Fumaric Acid" Agricultural and Biological Chemistry, vol. 25, No. 9, Jan. 1, 1961, pp. 726–730.

*Primary Examiner*—Herbert J. Lilling
*Attorney, Agent, or Firm*—Foley & Lardner

[57] ABSTRACT

A novel enzymatic, non-batch process for converting maleic acid to fumaric acid and/or producing L-aspartic acid, wherein dissolved oxygen concentration in the reaction medium in the reaction column or vessel is brought to 1 ppm (parts per million) or less with a deoxygenation agent and/or an inert gas, is provided.

14 Claims, No Drawings

PROCESS FOR PRODUCING L-ASPARTIC ACID

BACKGROUND OF THE INVENTION

1. Field of the Invention

The present invention relates to an enzymatic process for converting maleic acid to fumaric acid, characterized in that the lifetime of the enzyme used in the converting reaction is extended by lowering dissolved oxygen concentrations in the medium for the substrate. In addition, the present invention relates to a enzymatic process for producing L-aspartic acid by reacting maleic acid with ammonium, characterized in that the lifetime of the enzyme used in the reaction is extended by lowering the dissolved oxygen concentration in the medium for the substrate.

2. Related Art

It has been found out that the microorganisms that belong to genera of Pseudomonas, Bacillus, Aeobacter (Enterobacter) or Brervibacterium can convert maleic acid to fumaric acid (sees for example, Japanese Examined Patent Publication No. 42-11993, and Japanese Examined Patent Publication No. 42-11994). In general, in an enzymatic reaction, using an enzyme for a certain period of time necessitates exchanges of the enzyme due to inactivation of the enzyme. Such an inactivation is inevitable because of the fact that an enzyme is a proteinacious material. In particular, in the process for producing L-aspartic acid by reacting maleic acid with ammonium, the maleic acid-isomerizing enzyme used is prone to be inactivated by oxygen, therefore, the enzyme has to be exchanged quite frequently. A non-batch process using such an enzyme causes the cost of the facilities and the personnel to be high.

SUMMARY OF THE INVENTION

Thus, one object of the present invention is to provide an enzymatic process for converting maleic acid to fumaric acid, characterized in that it uses low cost raw materials, is simple, and can stably produce the product for the extended period of time.

Another object of the present invention is to provide an enzymatic process for producing L-aspartic acid by reacting maleic acid with ammonium, characterized in that it uses low cost raw materials, is simple, and can stably produce the product for the extended period of time.

The other objects of the present invention will be appreciated from the descriptions as set forth hereinafter with regard to the preferred embodiments thereof.

The present inventions are based in part on intensive studies on continuous bio-catalytic reactions in view of enzymatic kinetics.

According to one aspect of the present invention, the above object can be attained by an enzymatic process for converting maleic acid to fumaric acid by allowing maleic acid to be contacted with an enzymatic preparation comprising an enzyme having a maleic acid-isomerizing activity, characterized in that dissolved oxygen concentrations in the reaction medium in the reaction column or vessel are brought into 1 ppm (parts per million) or less with a deoxygenated agent and/or an inert gas.

According to another aspect of the present invention, the above object can be attained by an enzymatic process for producing L-aspartic acid by allowing a medium containing maleic acid and ammonium and/or maleic ammonium, to be contacted with an enzymatic preparation comprising an enzyme having both of maleic acid-isomerizing activity and aspartase (aspartate ammonia-lyase) activity, or with two enzymatic preparations, one comprising an enzyme having maleic acid-isomerizing activity and the other comprising an enzyme having aspartase (aspartate ammonia-lyase) activity, contained in a reaction column or vessel, characterized in that dissolved oxygen concentrations in the reaction medium in the column or vessel are brought into 1 ppm (parts par million) or less with a deoxygenated agent and/or an inert gas.

According to further aspect of the present invention, the above object can be attained by those processes in which the deoxygenated agent in the reaction medium is selected from the group consisting of sulfurous acid, sulfite and hydro-sulfite.

The entire disclosure of Japanese Patent Application No. 8-211595 filed on Aug. 9, 1996 including specification, claims and summary is incorporated herein by reference in its entity.

DETAILED DESCRIPTION OF THE PREFERRED EMBODIMENTS

The present invention is illustrated by the following embodiments, which, however, are not to be considered as limiting in any way the scope of protection.

The microorganisms for use within the present invention include, but are not to be limited to, for example, microorganisms that belong to the genus of Alcaligenes, such as *Alcaligenes faecalis* (ATCC No. 8750), Enterobacteriaceae, such as *Enterobacter aggromerans* (NSM-1), the genus of Citrobacter, such as *Cirobacter freundii* (NSM-2), the genus of Klebsiella, such as *Klebsiella planticola* (NSM-3), the genus of Pseudomonas, such as *Pseudomonas fluorescent* (NSM-4). A preferred microorganism for use within the present invention is one that enables higher yields for L-aspartic acid. *Enterobacter aggromerans* (NSM-1), *Cirobacter freundii* (NSM-2), *Klebsiella planticola* (NSM-3) and *Pseudomonas fluorescens* (NSM-4) were deposited at the National Institute of Bioscience and Human-Technology (NIBH) under the deposit Nos. FERM P-14447, FERM P-14448, FERM P-15144 and FERM P-15560, on Jul. 21, 1994, Jul. 21, 1994, Aug. 30, 1995 and Apr. 12, 1996, respectively, and transferred to the international depositories on Aug. 5, 1997 according to the Budapest Treaty. The deposit numbers under the Treaty are Nos. BP-6034, BP-6035, BP-6036 and BP-6037, respectively.

The taxonomic Characters of NSM-1 and NSM-2 are given in Table 1:

TABLE 1

| | strain | |
|---|---|---|
| items | NSM-1 | NSM-2 |
| morphology | short rod | short rod |
| motility | + | + |
| flagella | peripheral | peripheral |
| Gram staining | negative | negative |
| OF (Oxidation-fermentation)-test | fermentation | fermentation |
| yellow pigment | – | – |
| production of indole | +++ | – |
| VP (Voges-Proskauer) test | – | – |
| liquefiability of gelatin | – | – |
| formation of gas from | + | + |

TABLE 1-continued

| items | strain NSM-1 | NSM-2 |
|---|---|---|
| D-glucose formation of acid from: | | |
| D-glucose | +++ | +++ |
| D-mannitol | +++ | +++ |
| myo-inositol | – | – |
| D-sorbitol | +++ | +++ |
| L-rhamnose | +++ | +++ |
| sucrose | +++ | +++ |
| melibiose | – | – |
| L-amygdalin | +++ | +++ |
| L-arabinose | +++ | +++ |
| beta-galactosidase | +++ | +++ |
| arginine deiminase (arginine dihydrolase) | – | +/– |
| lysine decarboxylase | – | – |
| ornithine decarboxylase | – | – |
| utilization of citrate (Simmons medium) | +++ | +++ |
| production of hydrogen sulfide (TSI) | – | – |
| urease (Christensen' medium) | – | – |
| tryptophan deaminase | – | – |

TABLE 2

| items | strain NSM-3 |
|---|---|
| morphology | short rod |
| Gram staining | – |
| formation of spore | – |
| motility | – |
| form of colony | circular, entire, white, umbonate, smooth, glistening, translucent |
| growth at 37° C. | + |
| growth at 41° C. | + |
| catalase | + |
| oxidase | – |
| fermentability in glucose OF medium, rapid test (API) 30° C., 24 hours | + |
| beta-galactosidase | + |
| arginine deiminase (arginine dihydrolase) | – |
| lysine decarboxylase | + |
| ornithine decarboxylase | – |
| utilization of citrate | + |
| production of hydrogen sulfide | – |
| urease | + |
| tryptophan deaminase | – |
| production of indole | + |
| VP (Voges-Proskauer) test | (+) |
| gelatinase (pepsin B) | – |
| formation of acid from: | |
| glucose | + |
| mannitol | + |
| inositol | + |
| sorbitol | – |
| rhamnose | + |
| sucrose | + |
| melibiose | + |
| amygdalin | + |
| L(+)-arabinose | + |
| cytochrome oxidase (cytochrome-c oxidase) | – |
| reduction of nitrate | + |
| N$_2$ gas | – |

TABLE 2-continued

| items | strain NSM-3 |
|---|---|
| biochemical test: | |
| oxidation of gluconic acid | + |
| catabolic ability of m-hydroxy benzoic acid | – |
| melezitose PWS | – |
| sorbitol PWS | (+) trace |
| methyl red | + |
| dulcitol (galactitol) PWS | – |

(+): weakly positive
PWS: growth in peptone sugar aqueous solution

The inventors isolated NSM-4 from the soil in Tsukuba-city, Japan.

The taxonomic characters of NSM-4 are given in Table 3:

TABLE 3

| items | strain NSM-4 |
|---|---|
| morphology | short rod |
| Gram staining | – |
| Spores | – |
| Motility | + |
| form of colony | Round, regular, entire, cream with green fluorescent tinge, semi-translucent, low convex, smooth, glossy, 1–2 mm in diameter Pigment in King's B broth + |
| Growth at 37° C. | + |
| Growth at 41° C. | – |
| Catalase | + |
| Oxidase | + |
| Fermentative in Glucose OF Rapid Test (API) (30° C., 48 hr) | –(Oxidative) |
| NO$_3$ reduction | – |
| Indole production | – |
| Acid from glucose | – |
| Arginine dihydrolase | + |
| Urease | – |
| Aesculin hydrolysis | – |
| Gelatin hydrolysis | – |
| β-galactosidase | – |
| glucose assimilation | + |
| arabinose assimilation | + |
| mannose assimilation | + |
| mannitol assimilation | + |
| N-acetylglucosamine assimilation | – |
| maltose assimilation | – |
| caprate assimilation | + |
| adipate assimilation | – |
| malate assimilation | + |
| citrate assimilation | + |
| phenylacetate assimilation | – |
| cytochrome oxidase | + |
| Residual nitrate | + |
| Biochemical Test: | |
| Levan | – |
| Gelatin | – |
| Casein | – |
| Tween 80 | – |
| Acid from Maltose | Alkaline |
| Egg yolk opacity | + |
| Inositol csu | + |
| Sorbitol csu | + |
| Trehalose csu | + |

TABLE 3-continued

| items | strain NSM-4 |
| --- | --- |
| Benzylamine | − |
| Arginie dehydrolase | + |
| N$_2$ Reduction | − |

As a result of studying their bacteriological properties according to Bergey's Manual of Systematic Bacteriology, vol. 1–4, (1986), it was discovered that the strain of NSM-1 belongs to *Enterobacter aggromerans* in view of O-F test, VP test, qeneration of indole, generation of acid from various saccharides, availability of citrate, etc., the strain of NSM-2 belongs to *Citrobacter freundii* in view of O-F test, VP test, availability of citrate, generation of hydrogen sulfide, etc., the strain of NSM-3 belongs to *Klebsiella planticola* in view of mobility, urease test, availability of citrate, catabolic ability of m-hydroxy benzoic acid, methyl red test, and the strain of NSM-4 belongs to *Pseudomonas fluorescens* in view of Gram staining, motility +, OF test −, oxidase +, assimilation of saccharides, assimilation of organic acids, arginine dihydrolase +, production of fluorescent pigments, etc.

The microorganisms were collected from the culture medium by centrifugation or filtration, and then washed with water or another suitable buffer to give crude cells, which were used further in the reaction of the present invention. These crude cells may be physically and/or chemically treated, for example, may be subjected to sonication, grinding, freezing and thawing, or a detergent treatment, and then the resultant lyslate may be purified by salting out with sulfate ammonium, precipitation with acetone, or the like, to give the enzyme. By the term "enzymatic preparations", as used herein, are meant either microbial cell or cell lysate, or those immobilized with a suitable natural high molecular weight carrier, such as cellulose, alginic acid, kappa-carrageenan, or a suitable synthetic high molecular weight carrier, such as ion-exchange resin, polyacrylamide gel, in a conventional manner.

The carboxylic acid for use within the present invention, which may be the substrate of the enzyme, may be selected from the group consisting of maleic acid anhydride, maleic acid, and maleate. Preferably, a compound having SH groups, such as mercaptoethanol, glutathione, cystein, dithiothreitol, may be added to the reaction medium in the range of concentration from 0.1 to 50 mM, preferably, from 1 to 10 mM.

It has been found out that oxygen in the reaction medium may inactivate maleic acid-isomerase, aspartase, and the like, therefore, the SH groups-containing compound, such as mercaptoethanol has been added into the reaction medium. However, adding the compound alone has been found to be insufficient to block the inactivation. For this end, the inventors tried to decrease the dissolved oxygen concentrations in the reaction medium. As a result of these intensive tests, the inventors discovered that lowering the dissolved oxygen concentration enables the lifetime of the enzyme to be significantly extended.

The dissolved oxygen concentration may usually be 8 ppm at 25° C. in the reaction medium. Controlling the concentrations to 1 ppm or less, preferably, to 0.1 ppm or less, more preferably, to 0.01 ppm or less may be desirable to extend the lifetime of the enzyme. The method for removing dissolved oxygen in the medium for the substrate may be (1) to add a deoxygenated agent to the medium, and/or (2) to removing oxygen with an inert gas.

As the deoxygenated agent, sulfite ions may be used. The source of the sulfite ions may be sodium sulfite, potassium sulfite, ammonium sulfite, the salts of ammonium sulfite, etc. or sulfurous acid, or hydrosulfite, or any combinations thereof. Preferably, sulfite ions or a hydrosulfite may be added to the medium in the range of concentration from 20 ppm to 1%, preferably, from 100 ppm to 0.5%. The efficiency for removing oxygen by addition of sulfurous acid or sulfite may depend on the temperature of the reaction medium. If the temperature is below 20° C., the velocity of removal of oxygen would be low and the rate of removal of oxygen would be also low. On the other hand, if the temperature of the reaction medium is above 30° C., oxygen may be removed with considerable efficiency. The deoxygenated agent may be added to the reaction medium in a preparation tank when preparing the medium for the substrate, or in a storage tank for the medium, or in an inlet line to the reaction column or vessel. Particularly, hydrosulfite is advantageous when the reaction is carried out at lower temperature, since hydrosulfite may keep the rate of removal of oxygen high even at lower temperature.

In a process for lowering a dissolved oxygen concentration in the reaction medium by an inert gas, the inert gas may be nitrogen, argon, helium, or the like, or any combinations thereof. The inert gas may be charged into the storage vessel after the preparation of the reaction medium, and the gas phase in the storage vessel may be replaced with the charged inert gas to lower the dissolved oxygen concentration in the medium. Alternately, the inert gas may be introduced into the reaction medium to remove the dissolved oxygen. Any other suitable method may be used. In the case of replacing the gas phase in the storage vessel with the inert gas, the oxygen concentration in the gas phase may be less than 5%, preferably, less than 3%, more preferably, less than 1%. The material of the storage vessel for the reaction medium may be, but is not to be limited to, stainless steel, iron, plastics, glass. Preferably, the shape of the storage vessel may be, but is not to be limited to, the one in which the vessel can be closed with lid, or the vessel can retain the inert gas in the gas phase.

As mentioned above, the method for removing dissolved oxygen in the medium for the substrate may be (1) to add a deoxygenated agent to the medium, and/or (2) to removing oxygen with an inert gas. The combination of (1) with (2) may be more effective. The velocity of an enzymatic reaction is low at lower temperature because of its kinetics. Thus, to enable higher yields of the product at lower temperature, larger amounts of enzyme would be required. On the other hand, the enzymatic activity of maleic acid isomerase is prone to be lower at higher temperature. Thus, in order to suppress a decrease in its enzymatic activity, a higher temperature in the reaction column or vessel may not be desirable. Therefore, the temperature in the reaction column or vessel may be required to be in the range from 5 to 50° C., preferably, from 10 to 40° C., more preferably, from 15 to 35° C.

In another embodiment of the present invention, L-aspartic acid may be produced by a non-batch enzymatic process using the resultant fumaric acid and ammonium as well as an enzymatic preparation comprising an enzyme having aspartase (aspartate ammonia-lyase) activity. The microorganism having aspartase activity may be, but is not to be limited to, for example, a strain from the genus Escherichia, such as *Escherichia coli* (ATCC No. 11303, ATCC No. 9637, ATCC No. 7325), or a strain from the genus Brevibacterium.

In the process comprising the step of converting maleic acid to fumaric acid and the step of producing L-aspartic acid from the resultant fumaric acid, the concentrations of maleic acid as raw material may be preferably in the range from 5 to 40% by weight. Considering the solubility of the salt of maleic acid in the reaction medium and the reactivity of the bio-catalyst, the concentration of maleic acid in the medium may be advantageously in the range from 10 to 30% by weight, more preferably, from 10 to 25% by weight. In addition, a salt of a metal, for example, a salt of manganese, such as manganese chloride, manganese sulfate, etc., a salt of magnesium, such as magnesium chloride, magnesium sulfate, etc., or a salt of zinc, calcium, nickel, cobalt, or iron, etc. may be added to the reaction medium in the range of the concentrations from 0.1 to 50 mM, preferably, from 1 to 10 mM.

Thus, the present invention can provide an enzymatic, non-batch process for converting maleic acid to fumaric acid by allowing maleic acid to be contacted with an enzymatic preparation comprising an enzyme having a maleic acid-isomerizing activity, contained in the reaction column or vessel, characterized in that the raw material is continuously fed into the reaction column or vessel and the dissolved oxygen concentration in the reaction medium in the reaction column or vessel is lowered with a deoxygenated, agent and/or an inert gas.

Further, the present invention can provide an enzymatic, non-batch process for producing L-aspartic acid by allowing a medium containing maleic acid and ammonium and/or maleic ammonium, to be contacted with an enzymatic preparation comprising an enzyme having both of maleic acid-isomerizing activity and aspartase (aspartate ammonia-lyase) activity, or with two enzymatic preparations, one comprising an enzyme having maleic acid-isomerizing activity and the other comprising an enzyme having aspartase (aspartate ammonia-lyase) activity, contained in a reaction column or vessel, characterized in that the raw materials are continuously fed into the reaction column or vessel and the dissolved oxygen concentrations in the reaction medium in the column or vessel is lowered with a deoxygenated agent and/or an inert gas.

EXPERIMENTS

The present invention is illustrated in more detail by the following examples which, however, are not to be considered as limiting in any way the scope of protection.

EXAMPLE 1

100 ml of the medium shown in Table 4, which has been poured into in a Sakaguchi flask and sterilized, was inoculated with the strain *Enterobacter agglomerans* NSM-1 (FERM P-14447). After growth for 24 hours, one liter of the same medium, which had been charged in jar fermenter of volume of two liters and sterilized, was inoculated with the whole inoculant, and then allowed to culture at 30° C. with stirring and aeration. The pH of the medium was adjusted at pH 7.5 or below with 40% aqueous solution of maleic acid during the culture. After a growth of 8 hours, the microbial cells were collected by centrifugation at 10,000 rpm, and washed with 0.1M phosphate buffer, to which 200 ml of 0.1M phosphate buffer was added, and the microbial cells were disrupted by a homogenizer. The supernatant thus obtained was used as crude enzymatic solution. 1 ml of the crude enzymatic solution and 9 ml of solution of maleic acid containing the predetermined amount of sodium sulfite shown in Table 5, were placed in 20 ml test tube, shaken at 30° C., samples of the reaction medium were collected from the test tube at different times, and the samples were analyzed.

The results are shown in Table 6. Maleic acid decreased in the course of time, and was converted to fumaric acid and malic acid. With the system containing sodium sulfite, the activity of converting maleic acid was maintained even after 30 hours. In the case of 10 g/l of sodium sulfite, the dissolved oxygen concentration was 0 ppm.

TABLE 4

| Medium for Culturing Microbial Cells | |
|---|---|
| maleic acid | 10 g |
| ammonium sulfate | 5 g |
| monopotassium phosphate | 1 g |
| dipotassium phosphate | 3 g |
| sodium hydroxide | 5.5 g |
| magnesium sulfate | 0.5 g |
| Yeast Extract | 20 g |
| tap water 1 L, pH 6.2 | |

TABLE 5

| Composition of Medium for Maleic Acid | |
|---|---|
| maleic acid | 200 g |
| MgSO$_4$ | 0.25 g |
| mercaptoethanol | 0.78 g |
| sodium sulfite | 10 g |
| distilled water | 500 ml |
| adjusted to pH 7.2 with sodium hydroxide, and distilled water added up to 1 L of the final volume | |

TABLE 6

| | sodium sulfite | maleic acid remained (wt. %) hours | | | | O$_2$ cons. (ppm) hours | |
|---|---|---|---|---|---|---|---|
| | g/L | 0 | 5 | 20 | 30 | 0 | 30 |
| Example 1 | 10 | 9 | 5 | 2 | 0 | 0 | 0 |
| Comparative example 1 | 0 | 9 | 5 | 4 | 4 | 8 | 8 |

Comparative Example 1

An experiment similar to Example 1 was repeated except that the medium having a composition shown in Table 7 was used. The results ate shown in Table 6. Initially, maleic acid decreased in the course of time, and was converted to fumaric acid and malic acid. After 5 hours, the activity of converting maleic acid was extinguished. At the time, the oxygen concentration in the reaction medium was about 7.5 ppm.

TABLE 7

| Composition of Medium for Maleic Acid | |
|---|---|
| maleic acid | 200 g |
| MgSO$_4$ | 0.25 g |
| mercaptoethanol | 0.78 g |
| distilled water | 500 ml |
| adjusted to pH 7.2 with sodium hydroxide, and distilled water added up to 1 L of the final volume | |

EXAMPLE 2

An experiment similar to Example 1 was repeated except that the strain from *Citrobacter freundii* NSM-2 (FERM P-14448) was used. The results are shown in Table 8. The analysis on the reaction medium after a reaction time of 30 hours demonstrated that the resultant fumaric acid was 6.1% by weight and the resultant malic acid was 4.5% by weight, based on the medium.

TABLE 8

| | sodium sulfite | maleic acid remained (wt. %) hours | | | | $O_2$ cons. (ppm) hours | |
|---|---|---|---|---|---|---|---|
| | g/L | 0 | 5 | 20 | 30 | 0 | 30 |
| Example 2 | 10 | 9 | 5 | 3 | 0 | 0 | 0 |
| Comparative example 2 | 0 | 9 | 5 | 4 | 4 | 8 | 8 |

Comparative Example 2

An experiment similar to Example 2 was repeated except that the medium having composition shown in Table 7 was used. The results are shown in Table 8. Initially, maleic acid decreased in the course of time, and was converted to fumaric acid and malic acid. After 5 hours, the activity of converting maleic acid was extinguished. At the time; the oxygen concentration in the reaction medium was about 7.5 ppm.

EXAMPLE 3

A crude enzymatic solution of *Enterobacter agglomerans* NSM-1 (FERM P-14447) was prepared similarly to Example 1. 1 ml of the crude enzymatic solution and 9 ml of solution of ammonium maleate containing the predetermined amount of sodium sulfite shown in Table 9, were placed in 20 ml test tube, shaken at 30° C., samples of the reaction medium were collected from the test tube at different times, and the samples were analyzed.

The results are shown in Table 10. Maleic acid decreased in the course of time, and changed to L-aspartic acid. With the system containing sodium sulfite, the activity of converting maleic acid was maintained even after 30 hours. In the case of 1 g/L, 5 g/L, and 10 g/L of sodium sulfite, the oxygen concentrations were 1 ppm, 0 ppm and 0 ppm, respectively.

TABLE 9

Composition of Medium for Maleic Acid

| maleic acid | 200 g |
|---|---|
| 25% ammonia water | 200 g |
| MgSO$_4$ | 0.25 g |
| mercaptoethanol | 0.78 g |
| distilled water | 500 ml | adjusted to pH 8.3 with 1.5 g of sodium hydroxide or 10 g of ammonium, and distilled water added up to 1 L of the final volume

TABLE 10

| | sodium sulfite | maleic acid remained (wt. %) hours | | | | $O_2$ cons. (ppm) hours | |
|---|---|---|---|---|---|---|---|
| | g/L | 0 | 5 | 20 | 30 | 0 | 30 |
| Example 3 | 1 | 15 | 10 | 6.5 | 6 | 0 | 1 |
| | 5 | 16 | 10 | 6 | 5 | 0 | 0 |
| | 10 | 16 | 10 | 6 | 5 | 0 | 0 |
| Comparative example 3 | 0 | 16 | 10 | 9 | 9 | 8 | 8 |

TABLE 11

Composition of Medium for Maleic Acid

| maleic acid | 200 g |
|---|---|
| 25% ammonia water | 200 g |
| MgSO$_4$ | 0.25 g |
| mercaptoethanol | 0.78 g |
| distilled water | 500 ml | adjusted to pH 8.3 with ammonium, and distilled water added up to 1 L of the final volume

Comparative Example 3

An experiment similar to Example 3 was repeated except that the medium having composition shown in Table 11 was used. The results are shown in Table 10. Initially, maleic acid decreased in the course of time, and was changed to L-aspartic acid. After 5 hours, the activity of converting maleic acid was extinguished. The activity of aspartase was not inactivated after a reaction time of 30 hours. At the time, the oxygen concentration in the reaction medium was about 8 ppm.

EXAMPLE 4

A crude enzymatic solution of *Enterobacter agglomerans* NSM-1 (FERM P-14447) was prepared similarly to Example 1. 1 ml of the crude enzymatic solution and 9 ml of solution of maleic acid shown in Table 7, were placed in 20 ml test tube, the gas phase in the test tube was replaced with nitrogen, and then the test tube was sealed. While shaking the test tube at 30° C., samples of the reaction medium were collected from the test tube at different times, and the samples were analyzed. The replacing with nitrogen was conducted at each sampling time. The results are shown in Table 12.

TABLE 12

| | maleic acid remained (wt. %) hours | | | | $O_2$ cons. (ppm) hours | |
|---|---|---|---|---|---|---|
| | 0 | 5 | 20 | 30 | 0 | 30 |
| Example 4 | 16 | 10 | 6 | 5 | 0 | 0 |
| Comparative example 4 | 16 | 10 | 9 | 9 | 8 | 8 |

Comparative Example 4

An experiment similar to Example 2 was repeated except that the gas phase in the test tube was not replaced with nitrogen. The results are shown in Table 12.

EXAMPLE 5

100 ml of the medium shown in Table 4, which had been placed in a Sakaguchi flask and sterilized, was inoculated with the strain *Enterobacter agglomerans* NSM-1 (FERM P-14447). After a growth of 24 hours, 1 liter of the same medium, which had been charged in jar fermenter of volume of 2 liters and sterilized, was inoculated with the whole inoculant, and then allowed to grow at 30° C. with stirring and aeration. The pH of the medium was adjusted to pH 7.5 or below with a 40% aqueous solution of maleic acid during the culture. After a growth of 8 hours, the microbial cells were collected by centrifugation at 10,000 rpm, and washed with 0.1M phosphate buffer, to which 100 ml of a 3% aqueous solution of carrageenan was added and mixed with the microbial cells. The mixture was added in a droplet through a syringe into 500 ml of 2% aqueous solution of potassium chloride to form spherical gels about 4 mm in diameter. The immobilized microbial cells were thus prepared.

The immobilized microbial cells were packed into a column (10 cm in diameter, 30 cm in length) with the outer jackets, which had been controlled to 25° C. 1 L of aqueous solution of ammonium maleate shown in Table 13 was prepared, placed into 2 L glass bottle, and charged into the reaction column continuously at SV=0.2. The gas phase in the glass bottle was constantly replaced with a nitrogen flow. The reacted medium was sampled and analyzed. The results demonstrated that maleic acid was extinguished, and L-aspartic acid was produced at a concentration of 22.8% by weight based on the medium. The conversion rate of maleic acid to L-aspartic acid was 99% or more, and even after a reaction time of 2 days the conversion rate of maleic acid was 99% or more. The dissolved oxygen concentrations of aqueous solution of ammonium maleate at that time could not be detected.

TABLE 13

Composition of Medium for Maleic Acid

| | |
|---|---|
| maleic acid | 200 g |
| 25% ammonia water | 200 g |
| MgSO$_4$ | 0.25 g |
| mercaptoethanol | 0.78 g |
| sodium sulfite | 0.1 g |
| distilled water | 500 ml | adjusted to pH 8.3 with ammonium, and distilled water added up to 1 L of the final volume

Comparative Example 5

An experiment similar to Example 5 was repeated except that sodium sulfite was not added to the medium and the glass bottle with the medium was not sealed. The analysis on the reacted medium demonstrated that initially maleic acid was extinguished and changed to L-aspartic acid at a rate of 99% or more, however after a reaction time of 1 day the conversion rate of maleic acid was 0%.

EXAMPLE 6

100 ml of the medium shown in Table 14, which had been placed in a Sakaguchi flask and sterilized, was inoculated with the strain *Pseudomonas fluorescens* NSM-4 (FERM P-15560). After a growth of 24 hours, 1 liter of the same medium, which had been charged in jar fermenter of volume of 2 liters and sterilized, was inoculated with the whole inoculant and then allowed to grow at 30° C. with stirring and aeration. The pH of the medium was adjusted to pH 7.5 or below with a 40% aqueous solution of maleic acid during the culture. After a growth of 8 hours, the microbial cells were collected by centrifugation at 10,000 rpm, and washed with 0.1M phosphate buffer, to which 100 ml of a 3% aqueous solution of carrageenan at 40° C. was added and mixed with the microbial cells. The mixture was added in a droplet through a syringe into 500 ml of 2% aqueous solution of potassium chloride to form spherical gels about 4 mm in diameter. The immobilized microbial cells were thus prepared.

Measuring Method for Half Life

The resultant immobilized microbial cells were packed into a column with the outer jackets, which had been controlled to 30° C. by circulating hot water at the temperature of 30° C. through the outer jackets. 1 L of aqueous solution of ammonium maleate shown in Table 15 was prepared, placed into 2 L glass bottle with lid, and charged into the reaction column continuously at SV=0.2. The gas phase in the glass bottle was constantly replaced with a nitrogen flow. The reacted medium was sampled and analyzed after a reaction time of 12 hours.

The results demonstrated that the same amounts of L-aspartic acid as the extinguished maleic acid was produced. From the time when the conversion rate of maleic acid to L-aspartic acid reached no more than 90%, the conversion rates were determined by HPLC analysis, and how the conversion rates varied at different times was recorded. The gradient was obtained by plotting the logarithms of the conversion rates on the different reaction times, thereby the half-life of the enzymal activity converting maleic acid to L-aspartic acid was calculated to be 34.6 hours. The results are shown in Table 16.

TABLE 14

Medium for Culturing Microbial Cells

| | |
|---|---|
| maleic acid | 10 g |
| ammonium sulfate | 5 g |
| monopotassium phosphate | 1 g |
| dipotassium phosphate | 3 g |
| sodium hydroxide | 5.5 g |
| magnesium sulfate.7H$_2$O | 0.5 g |
| Yeast Extract | 20 g |
| tap water 1 L, pH 6.2 | |

TABLE 15

Composition of Medium for Maleic Acid

| | |
|---|---|
| maleic acid | 200 g |
| 25% ammonia water | 200 g |
| MgSO$_4$.7H$_2$O | 0.25 g |
| mercaptoethanol | 0.78 g |
| sodium sulfite | 10 g |
| distilled water | 500 ml | adjusted to pH 8.3 with ammonium, and distilled water added up to 1 L of the final volume

TABLE 15

Calculation of Converting Rate and Half Life in Column Reaction

| reaction time (hrs) | 12 | 118 | 135 | 168 |
|---|---|---|---|---|
| conversion rate (%) | 99.9 | 72.0 | 56.3 | 24.1 |
| log of the conversion rate | | 1.857 | 1.751 | 1.382 | gradient obtained by plotting the log of the conversin rates on the reaction times: −0.0087
correlation coefficient: $r^2 = 0.976$
half life of the active enzyme: −0.693/(−0.0087 × 2.303) = 334.6 (hrs)

EXAMPLE 7

A half life of the active enzyme was calculated to be 72.2 hrs similarly to Example 6 except that the medium for maleic acid shown in Table 17 was used.

TABLE 17

| Composition of Medium for Maleic Acid | |
|---|---|
| maleic acid | 200 g |
| 25% ammonia water | 200 g |
| MgSO$_4$ .7H$_2$O | 0.25 g |
| mercaptoethanol | 0.78 g |
| sodium hydrosulfite | 1 g |
| distilled water | 500 ml |
| adjusted to pH 8.3 with ammonium, and distilled water added up to 1 L of the final volume | |

We claim:

1. A process for converting maleic acid to fumaric acid comprising allowing maleic acid to be contacted with an enzymatic preparation and forming a reaction medium in a reaction column or vessel, the enzymatic preparation comprising an enzyme having a maleic acid-isomerizing activity, wherein the dissolved oxygen concentration in the reaction medium in the reaction column or vessel is brought to 1 ppm or less with a deoxygenation agent and/or an inert gas, and wherein said enzyme is derived from a microorganism selected from the group consisting of *Enterobacter agglomerans*, NSM-1; *Klebsiella planticola*, NSM-3; and *Pseudomonas fluorescens*, NSM-4.

2. The process according to claim 1, wherein a deoxygenation agent is used and is selected from the group consisting of sulfurous acid, sulfite and hydrosulfite.

3. A process for producing L-aspartic acid comprising allowing a medium containing maleic acid and ammonium and/or maleic ammonium, to be in contact with an enzymatic preparation comprising an enzyme having both maleic acid-isomerizing activity and aspartase activity, or with two enzymatic preparations, one comprising an enzyme having maleic acid-isomerizing activity and the other comprising an enzyme having aspartase activity, in a reaction column or vessel, wherein dissolved oxygen concentration in the reaction medium in the column or vessel is brought to 1 ppm or less with a deoxygenation agent and/or an inert gas, and wherein said enzyme having maleic acid isomerizing activity is derived from a microorganism selected from the group consisting of *Enterobacter agglomerans*, NSM-1; *Klebsiella planticola*, NSM-3; and *Pseudomonas fluorescens*, NSM-4.

4. The process according to claim 3, wherein the deoxygenation agent is used and is selected from the group consisting of sulfurous acid, a sulfite and a hydrosulfite.

5. A process according to claim 1, wherein the enzyme is derived from *Enterobacter agglomerans*, NSM-1.

6. A process according to claim 1, wherein the enzyme is derived from *Klebsiella planticola*, NSM-3.

7. A process according to claim 1, wherein the enzyme is derived from *Pseudomonas fluorescens*, NSM-4.

8. A process according to claim 3, wherein the enzyme is derived from *Enterobacter agglomerans*, NSM-1.

9. A process according to claim 3, wherein the enzyme is derived from *Klebsiella planticola*, NSM-3.

10. A process according to claim 3, wherein the enzyme is derived from *Pseudomonas fluorescens*, NSM-4.

11. A process according to claim 1, wherein said deoxygenation agent is used.

12. A process according to claim 1, wherein said inert gas is used.

13. A process according to claim 3, wherein said deoxygenation agent is used.

14. A process according to claim 3, wherein said inert gas is used.

* * * * *